United States Patent [19]

van der Heijden

[11] Patent Number: 5,000,383

[45] Date of Patent: Mar. 19, 1991

[54] VAPOR RELEASING DEVICE

[75] Inventor: Johannes van der Heijden, Hilversum, Netherlands

[73] Assignee: S. C. Johnson & Son, Inc., Racine, Wis.

[21] Appl. No.: 490,874

[22] Filed: Mar. 9, 1990

[51] Int. Cl.$^5$ .............................................. A61L 9/08
[52] U.S. Cl. ........................................ 239/47; 239/44
[58] Field of Search .................. 239/34, 43, 44, 47, 239/50, 53, 55, 51.5, 51, 52, 56, 57, 45

[56] References Cited

U.S. PATENT DOCUMENTS

| | | | |
|---|---|---|---|
| 3,587,968 | 6/1971 | Hennart et al. | 239/47 |
| 3,727,840 | 4/1973 | Nigro . | |
| 3,908,906 | 9/1975 | Crowle et al. . | |
| 3,976,246 | 8/1976 | Hauri et al. . | |
| 4,286,754 | 9/1981 | Jones | 239/44 |
| 4,526,320 | 7/1985 | von Philipp et al. . | |
| 4,621,768 | 11/1986 | Lhoste et al. . | |
| 4,663,315 | 5/1987 | Hasegawa et al. | 239/44 |
| 4,732,321 | 3/1988 | Dolan | 239/47 |
| 4,739,928 | 4/1988 | O'Neil . | |
| 4,928,881 | 5/1990 | Barlics et al. | 239/44 |

Primary Examiner—Andres Kashnikow
Assistant Examiner—Christopher G. Trainor

[57] ABSTRACT

An air freshening device having an openable outer housing that, when open, activates the air freshening device by pulling an emanator out of a fluid reservoir and, when closed, seals the fluid reservoir from either evaporation or leakage. The activation and deactivation are accomplished by the use of a hooking pin within the upper housing which engages the emanator portion and pulls the wicking stem of the emanator out of the fluid reservoir. An air channel is exposed in the open position and closed off in the closed position.

10 Claims, 4 Drawing Sheets

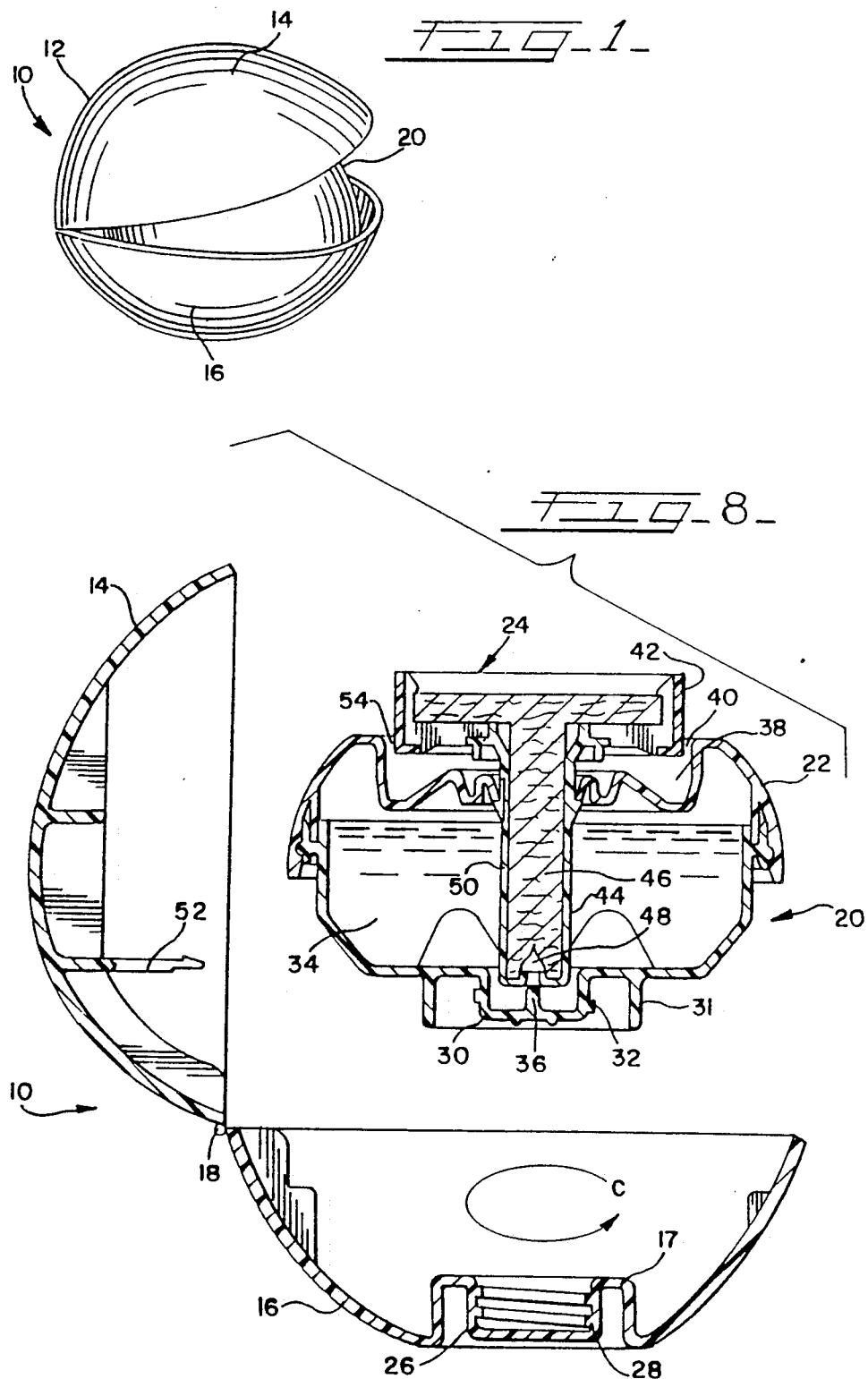

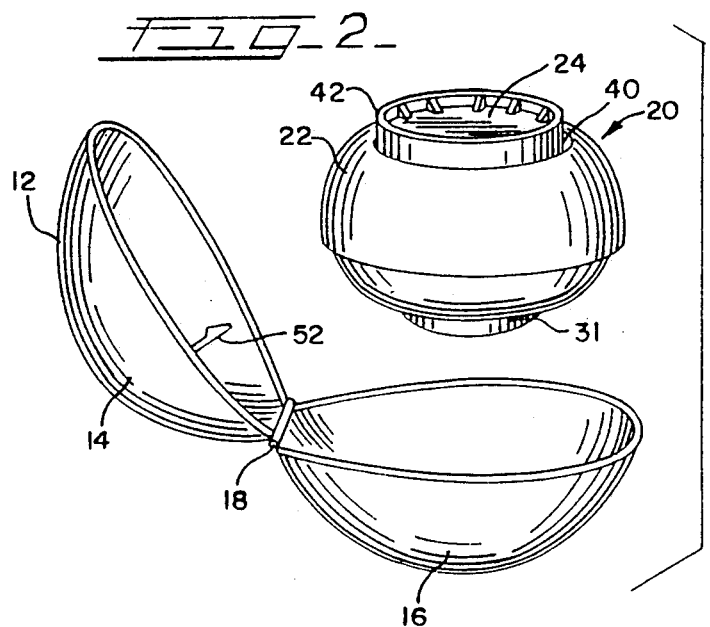
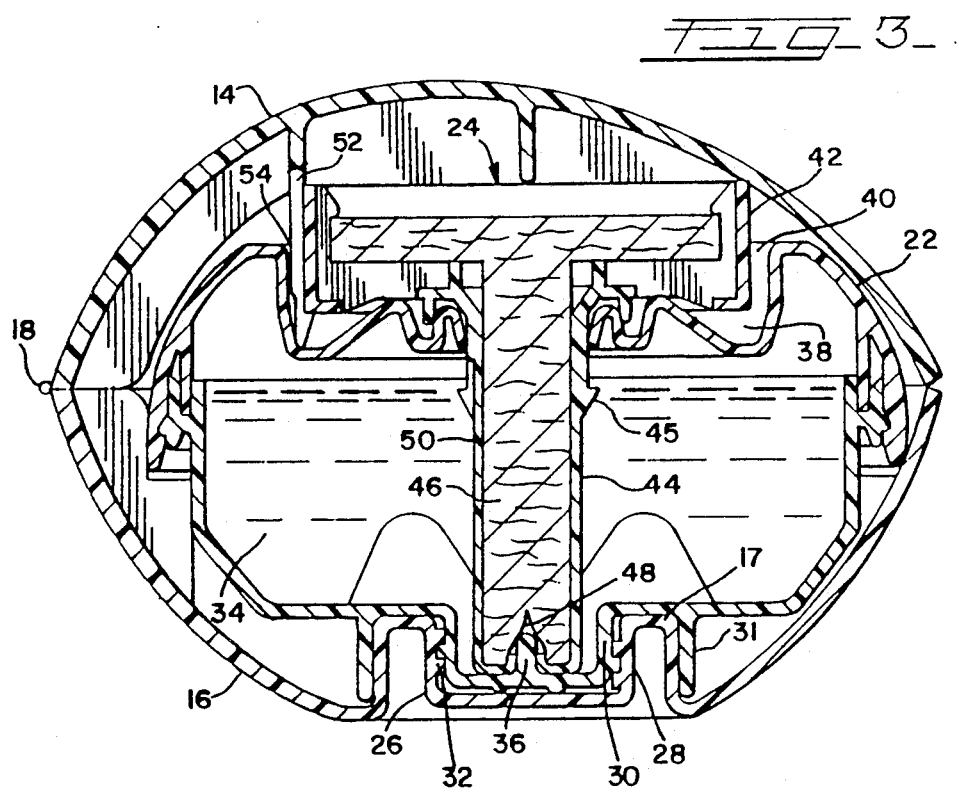

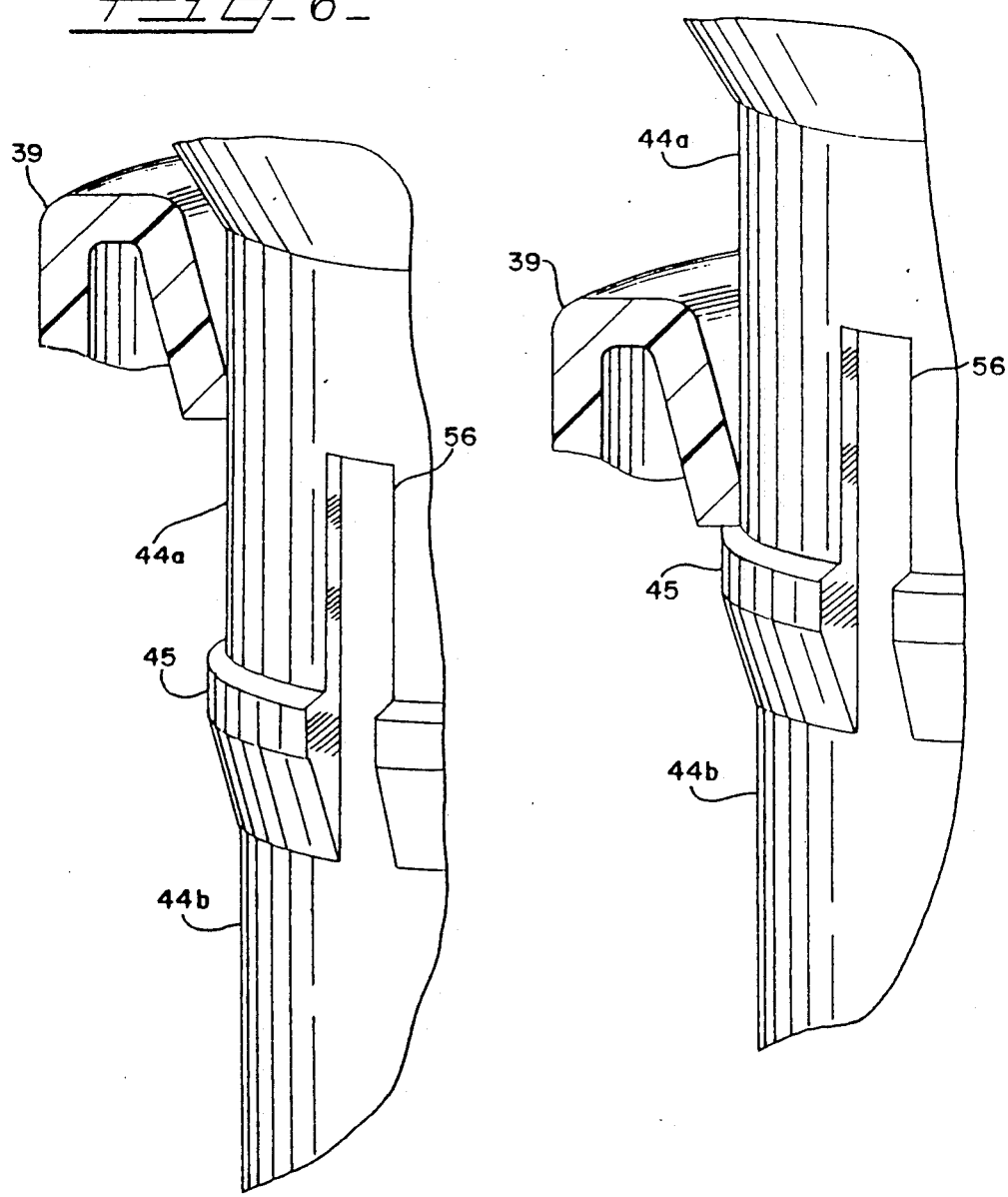

VAPOR RELEASING DEVICE

TECHNICAL FIELD

The present invention belongs to the field of containers that allow the release of vapors from fluid within the container and more particularly to such a device that has two main components: an outer openable housing and an inner fluid reservoir with a moveable wick and emanator system.

BACKGROUND OF THE INVENTION

Wick and container combinations designed to allow controlled evaporation of a volatile liquid are well known in the art. Most such combinations are intended to disperse a fragrant, deodorizing disinfecting, or even insecticidal, compound, into the atmosphere. Recent examples of this type include: U.S. Pat. No. 4,621,768 to Lhoste et al., "Device for Diffusing Volatile Liquids," discloses a fluid reservoir having a neck into which a wick fits in such a way that the wick is partially immersed in the liquid and extends beyond the mouth of the container. The device has a snap-on vented cover cup. U.S. Pat. No. 4,739,928 to O,Neill, "Air Freshener Dispenser," discloses a somewhat similar combination having, in addition to the wick, an emanator pad connected to the non-immersed portion of the wick, and a rotatable cover member. Rotation of the cover opens and closes the ventilation slits. In devices like these, the liquid in the container is always in contact with the wick. Even in a device like that of O'Neill, although most of the evaporation can be prevented by closure of the ventilating slits of the cover, volatile liquid still saturates the wick. The closure of the ventilating slits only retards further evaporation from the wick or emanator surface. A mechanism that actually seals off the volatile liquid reservoir when no evaporation is desired is disclosed by U.S. Pat. No. 3,727,840 to Nigro, "Dispersant Container and Dispenser." The container of this invention is formed with a threaded conical projection on the interior of a first apertured bottom portion of the container over which a second container shell portion, which actually holds the liquid, fits. Relative motion of the two portions opens and closes a channel between the projection and the opening of the second container shell allowing the liquid to reach (or be closed off from) a wicking material which lies along the interior surface of the first container portion. In any device intended in some manner to treat the ambient airspace, it is an advantage to have a device that is both attractive, since such devices are frequently placed in visible locations, and easily refillable. The ease of refill should be of two kinds: the refillable portion should be easy to remove and it should be refillable with little or no user contact with the contents which are usually of a concentration making direct contact somewhat unpleasant. In addition, such a device should have a mechanism by which the evaporation of the volatile liquid can be, by a sealing off of the liquid reservoir, prevented. No wick and container type evaporation device of the prior art combines all these advantages.

The present invention is a wick and container type evaporation device which has an outer, attractive container, an inner easily removeable and self-contained refill, and a means for alternately activating and deactivating the device. The advantages of the present invention over the prior art arise from the fact that when the outer container is closed, the inner reservoir is also closed in a leak-proof manner. When the outer container is opened up, a hooking mechanism engages and pulls the wick up out of the reservoir and opens up an air channel which allows sufficient air to enter the reservoir to allow the contents of the reservoir to travel up the wick by capillary action and ultimately evaporate from an emanator pad at the top of the wick. The outer container may be reclosed, again resealing off the reservoir and preventing further evaporation or possible leakage (which might occur if such a device were invented and lacked the closure means of the present invention).

BRIEF DESCRIPTION OF THE DRAWINGS

FIG. 1 is a perspective drawing of the assembled vapor releasing device in the partially opened or activated position.

FIG. 2 is a perspective drawing of the vapor releasing device showing the housing fully opened and the reservoir with its wick and emanator system positioned above the housing.

FIG. 3 is a side sectional view, taken along line A—A of FIG. 1, of the assembled vapor releasing device showing the housing in the closed position.

FIG. 6 is an enlarged partially in perspective and partially sectional view of the air channel of the device in the closed position.

FIG. 7 is an enlarged partially in perspective and partially sectional view of the air channel of the device in the open position.

FIG. 8 is a partially exploded side sectional view of the vapor releasing device, taken along line B—B of FIG. 2, showing the housing fully opened with the reservoir, including the wick and emanator system detached from the housing.

BEST MODE FOR CARRYING OUT THE INVENTION

Figure 4:
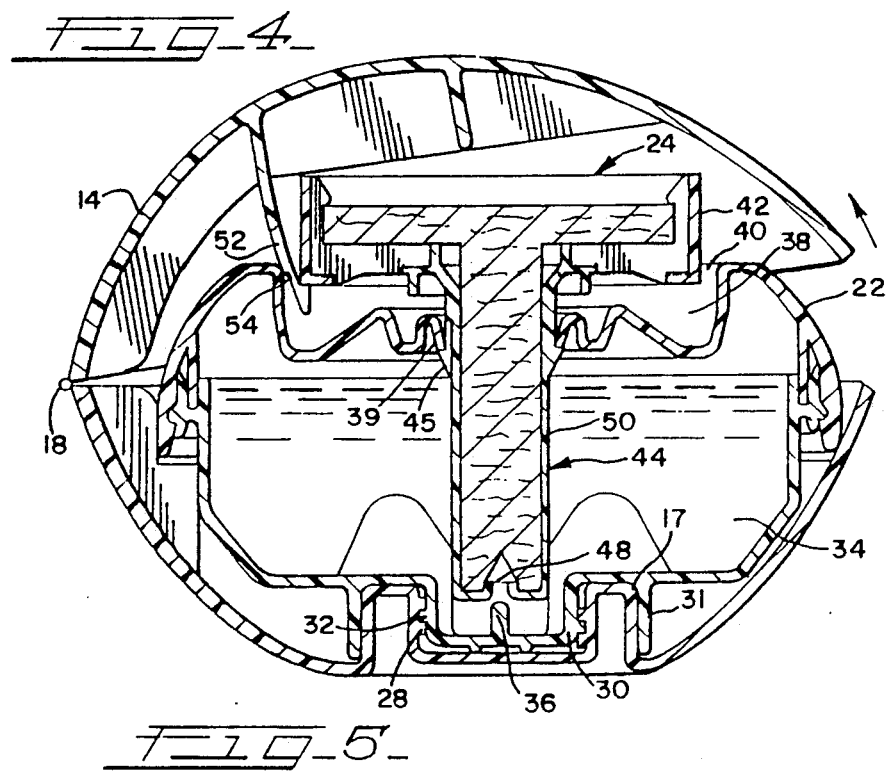
FIG. 4 is a side sectional view of the assembled vapor releasing device, taken along line A—A of FIG. 1, showing the housing in the partially opened or activated position.

FIG. 1 shows vapor releasing device 10 with openable housing 12, having upper housing portion 14 and lower or base housing portion 16, which are joined along one edge by hinging mechanism 18 (visible in later figures). Partially visible inside openable housing 12 is fluid reservoir 22 (visible in later figures) of fluid containing and emanating system 20.

In this figure, openable housing 12 is in the partially-opened position, in which fluid containing and emanating system 20 has been activated, as will be explained below. Openable housing 12 can, of course, be formed in almost any desired shape or color, so long as the configuration allows the housing to be opened for insertion of fluid containing and emanating system 20. One possible design for the housing of the present invention, that of a two-part shell-like structure, is disclosed by pending U.K. Design Pat. No. 1,057,656, filed Mar. 6, 1989.

FIG. 2 shows vapor releasing device 10 with openable housing 12 in its fully opened position. Hinging mechanism 18 is visible in this figure. Fluid containing and emanating system 20, which has fluid reservoir 22 and wicking and emanating element 24, is positioned above base housing portion 16 of openable housing 12. This is the orientation from which entire fluid containing and emanating system 20 would be lowered into base housing portion 16 when vapor releasing device 10 is initially assembled, or removed for replacement and refill, as described below.

Activation of the device and description of its functional parts will be discussed in connection with FIGS. 3, 4, 5 and 8, all of which show the same parts, but in different positions.

FIG. 3 shows the assembled vapor releasing device 10 with openable housing 12 in its completely closed position, the position in which the entire unit would be shipped and sold and into which it would be repositioned for temporary inactivation.

Formed into base housing portion 16 of openable housing 12 is a first attachment structure which, in this embodiment, is a central well structure 26 having on its inner surface internal screw threads 28. Fluid reservoir 22 has, on its lower surface, a second attachment structure, in this embodiment, a circular projection portion 30 having external screw threads 32 designed to mate with internal screw threads 28 within well structure 26 of base housing portion 16 of openable housing 12. Other means, such as bayonet lugs or undercut snap beads could also be used to detachably connect the reservoir to the housing. Circular projecting portion 30 is surrounded by circular reservoir ring 31, designed to fit over circular base housing structure 17 formed within base housing portion 16.

This attachment system allows fluid containing and emanating system 20 to be removably screwed into place within openable housing 12. However, should such removability not be desired, as would be the case were the device to be intended for one-time use, instead of having a replaceable wicking and emanating element, the attachment system could be a snap-fit or adhesive arrangement.

For manufacture and sale of this embodiment, fluid containing and emanating system 20 would be filled with fluid 34, which would probably be a solution carrying a volatile fragrant compound suitable for use in an air freshener, and then assembled. Other active ingredients such as pesticides or insect repellents could also be included. Then the fluid containing and emanating system 20 would be inserted into openable housing 12, and openable housing 12 would then be closed. For activation and use of the device, openable housing 12 would be partially opened, which would cause wicking and emanating element 24 of fluid containing and emanating system 20 raised from within and elevated above fluid reservoir 22, as will be described below.

Situated on and projecting upwards from the interior of fluid reservoir 22 and, in this embodiment, located within circular projection portion 30 of fluid reservoir 22, is closure pin 36. Fluid reservoir 22 is formed with central recess 38 in its upper surface. Within central recess 38 is neck opening 40 to the interior of fluid reservoir 22. Neck opening 40 has around its inner circumference innerly projecting sealing flange 39. Wicking and emanating element 24 has emanator portion 42 and, extending downwards therefrom, wicking leg 44. Encircling the outer surface of wicking leg 44 is collar 45. Wicking and emanating element 24 itself is made of central core of porous material 46, which has external coating of impermeable material 50 around the side of wicking leg 44 and the outer circumference of emanator portion 42. At one end of wicking leg 44 is inlet opening 48 which extends upwardly into central core of porous material 46.

When fluid containing and emanating system 20 is assembled, wicking leg 44 of wicking and emanating element 24 is inserted through neck opening 40 into fluid reservoir 22. The emanator portion 42 of wicking and emanating element 24 rests within central recess 3B formed into the top of fluid reservoir 22. When element 24 is fully inserted into reservoir 22, closure pin 36 located upon the interior of fluid reservoir 22 fits into inlet opening 48 on the bottom of wicking leg 44 of element 24. In this position, fluid 34 cannot reach central core of porous material 46 from which it would otherwise eventually evaporate.

Formed within and pendant from upper housing portion 14 of openable housing 12 is flexible hooking pin 52. When openable housing 12 is fully closed, hooking pin 52 rests in a non-flexed position within pin channel 54, which is formed between one edge of central recess 38 and one end of emanator portion 42 of wicking and emanating element 24.

As is shown in FIG. 4, when upper housing portion 14 of openable housing 12 is moved away from base housing portion 16, hooking pin 52 is pulled upwards and against the edge of central recess 38, which results in hooking pin 52 being slightly flexed and curving further under one end of emanator portion 42. As upper housing portion 14 is opened further, hooking pin 52 then pulls emanator portion 42 up and away from its position within central recess 38 of fluid reservoir 22. As shown in FIGS. 3 through 5 and 8, collar 45, formed around the circumference of wicking leg 44, contacts sealing flange 39 of central recess 38 when the device has been opened to the activated position. This prevents wicking and emanating element 24 from being pulled further from within fluid reservoir 22. When emanator portion 42 is pulled upwards, wicking leg 44 is moved away from its contact with closure pin 36. Fluid 34 is then able to make contact with central core of porous material 46 of wicking and emanating element 24. Fluid 34 then travels by capillary action up central core of porous material 46 of wicking leg 44 and into that portion of central core of porous material 46 which lies within emanator portion 42. When fluid 34 reaches the upper surface of that portion of central core of porous material 46 which lies within emanator portion 42, fluid 34 comes into contact with the atmosphere and evaporates, releasing the active ingredient into the surrounding area.

This activation process can be reversed by the user if no further evaporation from the device is desired. When openable housing 12 is closed by relative pressure on upper housing portion 14, emanator portion 42 is forced, by contact with the inner surface of upper housing portion 14 of openable housing 12, back into central recess 38 of fluid reservoir 22. When this occurs, hooking pin 52 slides back into position in pin channel 54 where, it again rests in its non-flexed position. At the same time, inlet opening 48, at the end of wicking leg 44, is pushed against closure pin 36, cutting off further contact of fluid 34 with central core of porous material 46 of wicking and emanating element 24.

When fluid 34 has all evaporated from within fluid reservoir 22, the entire fluid containing and emanating system 20 can, in this embodiment, be removed and replaced by a new fluid and emanating system 20. This process is shown in FIGS. 5 and 8.

Figure 5:
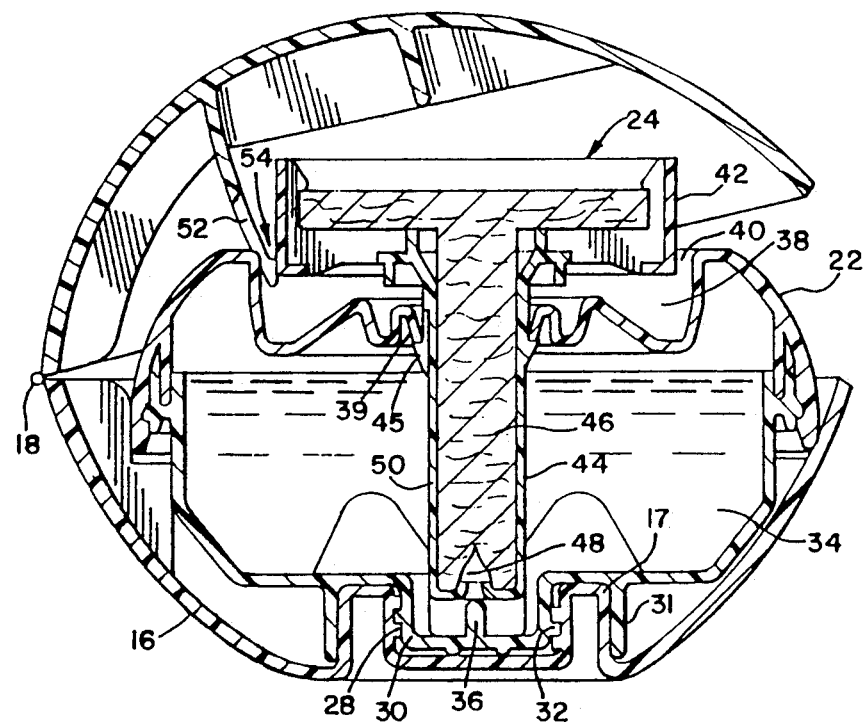
FIG. 5 is a side sectional view of the assembled vapor releasing device, taken along line A—A of FIG. 1, showing the housing in a position intermediate between the partially open position and the fully open position.

In FIG. 5, openable housing 12 has been more fully opened than the partially opened, activated position shown in FIGS. 1 and 4. As upper housing portion 14 of openable housing 12 is further separated from base housing portion 16, hooking pin 52 slips out from under the edge of emanator portion 42, allowing unrestricted opening of openable housing 12.

Without a means to allow air to reach the inside of fluid reservoir 22, when vapor releasing device 10 is in the open position, as described before, fluid 34 in fluid reservoir 22 would travel up core of porous material 46 of wicking leg 44 and evaporate from emanator portion 42, but would eventually, with no atmospheric pressure upon fluid 34, cease to so do.

Thus, a means for admitting air to the inside of fluid reservoir 22 is necessary. In the present embodiment of the invention, as shown in FIGS. 6 and 7, this means is a shallow air groove 56 axially located along the outside surface of wicking leg 44. Wicking leg 44 has two segments of slightly differing diameters (too small a difference to be visible in the sectional figures but visible in FIGS. 6 and 7, which are enlarged detail views.) The upper portion of wicking leg 44, upper wicking leg segment 44a has a slightly (0.3 mm. in the preferred embodiment of the invention) greater diameter than does the lower portion of wicking leg 44, lower wicking leg segment 44b. Air groove 56 bisects collar 45 to the depth of the diameter of lower wicking leg segment 44b. Air groove 56 then extends upwardly into upper wicking leg segment 44a, having a depth equal to the diameter of lower wicking leg segment 44b.

When vapor releasing device 10 is in its closed position, as shown in FIG. 6 (and FIG. 3) sealing flange 39 surrounds upper wicking leg segment 44a in a position above the upper end of air groove 56. Thus, fluid reservoir 22 is sealed by an air and fluid tight seal, as sealing flange 39 surrounds upper wicking leg segment 44a.

When vapor releasing device 10 is in its open position as shown in FIGS. 6 and 7 (and in FIGS. 5 and 8), wicking leg 44 is pulled up from its former location within fluid reservoir 22, as described earlier. Sealing flange 39 then rests on top of and against collar 45, and air groove 56 now has openings both above and below sealing flange 39 - allowing ambient air to enter fluid reservoir 22 and to allow continued capillary transport and evaporation of fluid 34.

When openable housing 12 has been fully opened, as shown in FIG. 8, fluid containing and emanating system 20 can be removed from its position within base housing portion 16 of openable housing 12. In the preferred embodiment, this is done by unscrewing fluid containing and emanating system 20 from base housing portion 16 as indicated by the direction of arrow C on FIG. 8.

Although the preferred embodiment illustrated and discussed above has flexible hooking pin 52 that engages the underside of the emanator portion 42 of vapor releasing device 10, other engaging and lifting mechanisms may be employed. For example, the hooking pin may be designed to slide and engage a key slot in the emanator portion itself, or the pin may be formed so as to interlock with an appropriately shaped slot in the emanator portion, or the pin may have, instead of a hook, a ball end, designed to be engaged by a socket within the emanator portion.

INDUSTRIAL APPLICABILITY

The vapor releasing device of the present invention is primarily intended for use as an air freshening device for the home or other enclosed space. For such use, the active ingredient in the solution in the reservoir would be a perfume. However, if the active ingredient were an insect repelling substance, the device could also be used as an insect repelling device.

Other modifications of the vapor releasing device of the present invention will become apparent to those skilled in the art from an examination of the above patent Specification and drawings. Therefore, other variations of the present invention may be made which fall within the scope of the following claims even though such variations were not specifically discussed above.

What I claim:

1. A vapor releasing device comprising:
    an openable housing having upper and lower portions and having a fluid containing and emanating system located therein;
    the fluid containing and emanating system further comprising:
    a fluid reservoir, designed to be removably fitted within the openable housing and having a top end and a bottom end, with a neck opening at its top end, and, inside the fluid reservoir and located at its bottom end, a closure pin;
    a wicking and emanating element formed of a central core of porous material with an external impermeable coating on portions thereof having a T-shaped configuration, the vertical portion of the T-shaped wicking and emanating element being designed to fit slidably into the neck opening of the fluid reservoir, and to extend downwardly therein so that, at maximum penetration, the bottom of the vertical portion of the T-shaped element mates with the closure pin of the reservoir, while the horizontal portion of the T-shaped element extends across and above the neck of the fluid reservoir.

2. A vapor releasing device according to claim 1 wherein the openable housing has an engaging and lifting mechanism comprising a flexible hooking pin extending from an interior surface of the openable housing and configured so that, when the openable housing is in a closed position, the hooking pin rests beneath one area of the underside of the horizontal portion of the T-shaped wicking and emanating element and, as the openable housing is being placed in an open position, the hooking pin pulls the wicking and emanating element upwards and slides the vertical portion of the wicking and emanating element partially out of the neck opening of the fluid reservoir and out of contact with the closure pin within the fluid reservoir, which allows fluid from the fluid reservoir to reach the central core of porous material of the wicking and emanating element, thereby activating the device by allowing the fluid to travel up the central core of porous material of the vertical portion of the wicking and emanating element to the vertical portion of the wicking and emanating element and then diffuse into the atmosphere.

3. A device according to claim 2 wherein the fluid reservoir has a recess formed into its upper surface, the recess being configured so that, when the housing is in the closed position, the horizontal portion of the T-shaped wicking and emanating element fits therein, the recess and the horizontal portion of the wicking and emanating element being so configured that a channel is formed between them in such an orientation that the hooking pin extending from the interior surface of the housing slidably fits into the channel and is thereby guided to engage and hook an area of the underside of the horizontal portion of the wicking emanating element.

4. A vapor releasing element according to claim 2 wherein the neck opening of the fluid reservoir has an innerly projecting flange that contacts and encircles the vertical portion of the T-shaped wicking and emanating element and the vertical portion of the wicking and emanating element has, encircling its outer surface, a collar structure, the collar structure being interrupted at least one point by a groove running transversely therethrough, the groove extending into the main body of the vertical portion of the wicking and emanating element, the collar and groove therethrough being so located that when the openable housing is in the closed position, the innerly projecting flange rests around the circumference of the vertical portion of the wicking and emanating element at a distance above the collar structure and the groove and, when the openable housing is in the open position, the innerly projecting flange is in contact with the collar structure and the groove so that air present above the neck opening of the reservoir can pass through the groove in the collar structure and enter the interior of the reservoir.

5. A device according to claim 4 wherein the vertical portion of the T-shaped wicking and emanating element has an upper segment of a slightly larger diameter than a lower segment and the groove bisects the collar structure to the depth of the surface of the lower segment of the vertical portion, the groove extending at the same depth into the upper segment, the groove and the innerly projecting flange being so located that, when the openable housing is in the closed position, the innerly projecting flange encircles the upper segment of the vertical portion of the wicking and emanating element above the groove, the innerly projecting flange and the vertical portion of the wicking and emanating element, thus sealing the fluid reservoir, and, when the openable housing is in the open position, the flange encircles the upper segment of the vertical portion of the wicking and emanating element below the groove, thus allowing air to enter the top of the groove and thence to enter the fluid reservoir.

6. A device according to claim 1 wherein the openable housing has within its lower portion a first attachment means designed to connect with a second attachment means on the bottom end of the fluid reservoir.

7. A device according to claim 3 wherein the openable housing has within its lower portion a first attachment means designed to connect with a second attachment means on the bottom end of the fluid reservoir.

8. A device according to claim 6 wherein the first attachment means is a recess having a set of internal screw threads therein and the second attachment means is a projection across the bottom of the fluid reservoir having a corresponding set of external screw threads thereupon.

9. A device according to claim 7 wherein the first attachment means is a recess having a set of internal screw threads therein and the second attachment means is a projection across the bottom of the fluid reservoir having a corresponding set of external screw threads thereupon.

10. A device according to claim 1 wherein the upper and lower portions of the openable housing are joined along one edge by a hinging mechanism.

* * * * *